United States Patent [19]
Payne et al.

[11] Patent Number: 5,224,934
[45] Date of Patent: Jul. 6, 1993

[54] PATIENT CONTROLLED BOLUS DOSAGE INFUSER

[75] Inventors: Steven R. Payne, San Diego; Frederic P. Field, Solana Beach; James M. Verespej, Carlsbad, all of Calif.

[73] Assignee: Block Medical, Inc., Carlsbad, Calif.

[21] Appl. No.: 802,885

[22] Filed: Dec. 6, 1991

[51] Int. Cl.⁵ .................................. A61M 37/00
[52] U.S. Cl. ........................... 604/132; 604/131
[58] Field of Search ............ 604/132, 131, 150, 123, 604/183, 185, 186, 122

[56] References Cited

U.S. PATENT DOCUMENTS

| | | | |
|---|---|---|---|
| 515,288 | 2/1894 | Harsin | 604/132 |
| 4,568,333 | 2/1986 | Sawyer et al. | 604/122 |
| 4,722,731 | 2/1988 | Vailancourt | 604/122 |
| 4,998,918 | 3/1991 | Mimura | 604/132 |
| 5,011,477 | 4/1991 | Winchell et al. | 604/132 |
| 5,014,750 | 5/1991 | Winchell et al. | 138/43 |
| 5,033,714 | 7/1991 | Winchell et al. | 251/127 |
| 5,080,652 | 1/1992 | Sancoff et al. | 604/132 |

Primary Examiner—John J. Wilson
Assistant Examiner—Jeffrey A. Smith
Attorney, Agent, or Firm—Baker, Maxham, Jester & Meador

[57] ABSTRACT

An infusion system for the delivery of a first continuous flow of a intravenous fluid and second multiple selectable dosages of the fluid from a source to a site comprises a source of intravenous fluid under pressure, a housing having an inlet for connection to the source of fluid and an outlet for connection to a delivery site, a first passage in the housing for conveying a continuous constant low volume of the fluid to the outlet, and a second passage in the housing having an accumulator for accumulating a predetermined fixed charge of fluid and an actuator for selectively releasing the flow of the fluid from the accumulator to the outlet.

19 Claims, 2 Drawing Sheets

PATIENT CONTROLLED BOLUS DOSAGE INFUSER

BACKGROUND OF THE INVENTION

The present invention relates to medical infusion devices, and more particularly, to an improved combination continuous dose and bolus dose infusion system for delivering patient selectable controlled doses of intravenous drugs at controlled intervals above a controlled rate.

It is often necessary to intravenously supply patients with doses of pharmaceutically active liquids over a long period of time at a controlled rate. It is desirable that this be accomplished while the patient is in an ambulatory state.

The administration of effective doses of analgesics is highly subjective and depends on such factors as age, pain tolerance, renal function and other medications. For this reason, it is desirable that the patient have a certain amount of control over the dosage. However, it is also desirable that overdose be prevented. Many devices have been available in the past for allowing the self administration of analgesics. However, these have many drawbacks, including being bulky, complicated and expensive. Most of such devices also provide only an on demand rush of the drug.

One prior art infusion apparatus having many desirable characteristics is disclosed in U.S. Pat. No. 5,011,477, issued Apr. 30, 1991, to Winchell et al. This apparatus provides a combination of a continuous dose and a patient controlled bolus dose The device has the drawback of being complicated and expensive to manufacture.

Accordingly, it would be desirable to provide an improved low cost patient controlled analgesic infusion system for delivering intravenous drugs in a continuous background dosage, with the ability for patient selection of a bolus dose substantially on demand.

SUMMARY OF THE INVENTION

It is, therefore, the primary object of the present invention to provide an improved low cost patient controlled analgesic infusion system for delivering intravenous drugs in a continuous background dosage, with the ability for patient selection of a bolus dose substantially on demand.

A primary aspect of the invention comprises a continuous source of intravenous fluid, with an in line controller for providing a continuous background dose, and an accumulator with a patient activated valve for providing a bolus dose substantially on demand.

BRIEF DESCRIPTION OF THE DRAWINGS

The above and other objects and advantages of the present invention will become apparent from the following description when read in conjunction with the accompanying drawings wherein.

DETAILED DESCRIPTION OF A PREFERRED EMBODIMENT

Figure 1:
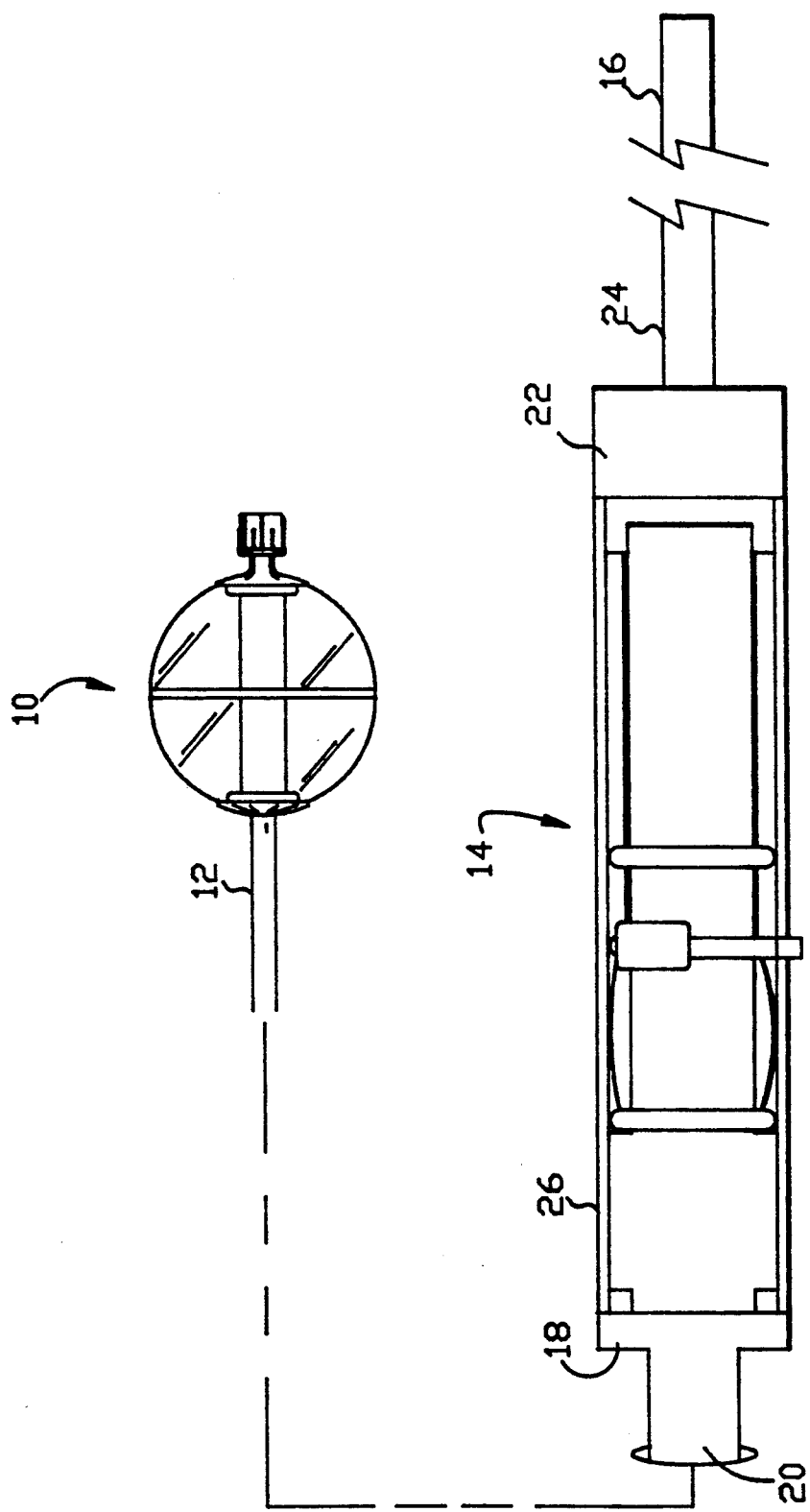
FIG. 1 is a front elevation view of a preferred embodiment of the invention.
Figure 2:
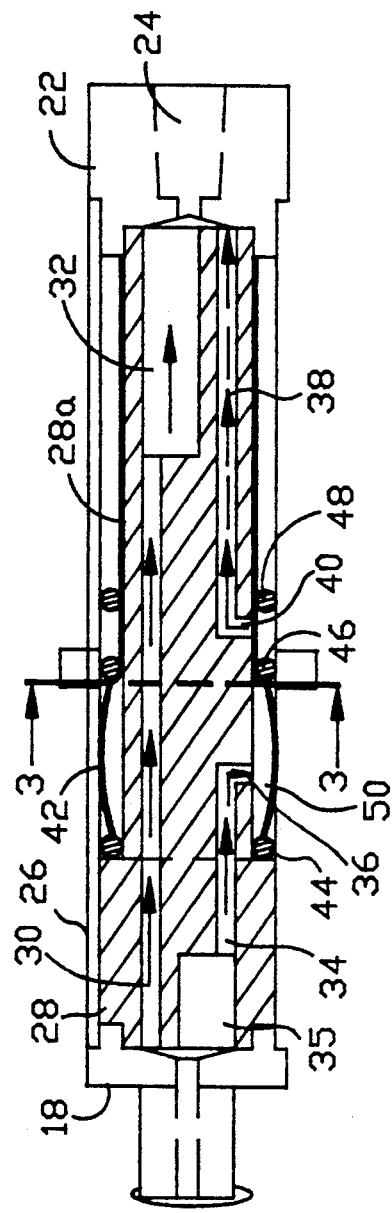
FIG. 2 is a sectional view of the fluid flow regulator of FIG. 1 showing details of construction and a first condition of the unit.

Referring to FIG. 1 of the drawing, there is illustrated an infusion system in accordance with the invention comprising a source of pressurized fluid, designated generally by the numeral 10, connected by way of the usual IV tubing 12 to a flow regulator device, designated generally at 14, for controlling the flow of an intravenous fluid by way of delivery tubing 16 to a patient. The system is designed as a patient controlled analgesic infusion device wherein the patient receives a first or continuous low level dosage of an analgesic and may periodically select a bolus dosage as needed. The device is designed as a simple and inexpensive disposable unit that is simple, reliable and easy to use. The source of pressurized fluid 10 is preferably an inflatable bladder infusor of such as disclosed in application Ser. No. 07/492,982, filed Mar. 12, 1990, now U.S. Pat. No. 5,080,652, and entitled "Infusion Apparatus", said application incorporated herein by reference as though fully set forth.

The control unit 14 comprises a housing, which in the illustrated embodiment has a generally cylindrical configuration having an inlet end wall 18, with an inlet port or connection 20 connected to the source of fluid 10 by tubing 12. An outlet end wall 22 includes an outlet port 24 connected by IV tubing 16 to a patient. A transparent tubular shell or sleeve 26 is connected between the end wall members 18 and 22, and forms a generally cylindrical chamber within which is disposed a centrally generally step cylindrical body member 28, forming an elongated annular chamber extending coaxially of the housing.

The flow control unit 14 has means for providing a first fixed continuous flow of fluid therethrough at a first predetermined rate. This first means comprises a first passageway 30 communicating between the inlet port 20 and an outlet port 24 by way of chamber 32 in which is mounted a metering orifice or capillary tube to provide a fixed continuous rate of flow. This is typically on the order of 0.5, 1.0 and 1.5 ml/hr and may be called or termed a background flow.

Second means for providing a bolus dosage comprises a second inlet passage 34 communicating by means of a port 36, with an outer surface of a reduced diameter portion of the support member 28. A chamber of cavity 35 is provided to receive an orifice or capillary tube to regulate the flow to fill the bolus reservoir at predetermined periods, such as 6, 15 or 60 minutes. An outlet passage 38 includes a port 40 communicating from the surface of the cylindrical portion 28a of the central member. The ports 36 and 40 are axially spaced apart and are covered by means of an elastic sleeve 42, which is preferably of silicone rubber and is sealingly secured by suitable means, such as a plurality of O-rings 44, 46 and 48 spaced axially along the tubular sleeve and cylindrical member 28a.

The combination of the tubular elastic sleeve and the O-rings form a bolus or accumulating reservoir 50 communicating initially solely with the inlet port 36 of the inlet passage 34. This provides an accumulation reservoir which accumulates a predetermined charge or dosage of the medication.

An extended portion of the elastic sleeve 42 extends over and covers outlet port 40 between O-rings 46 and 48. Thus, initially the chamber 50 is sealed from the outlet and accumulates a charge of fluid by expanding within the annular chamber. In a preferred form, the accumulation reservoir 50 fills within a predetermined period of time, such as fifteen minutes or any other selected period of time.

Means are provided to release the accumulated fluid into the adjacent chamber wherein it may flow via outlet port 40 and passage 38 to the outlet 24.

Figure 3:
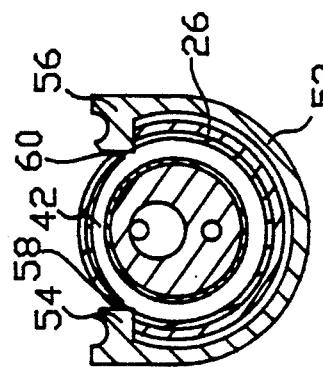
FIG. 3 is a section view taken on line 3—3 of FIG. 2.
Figure 4:
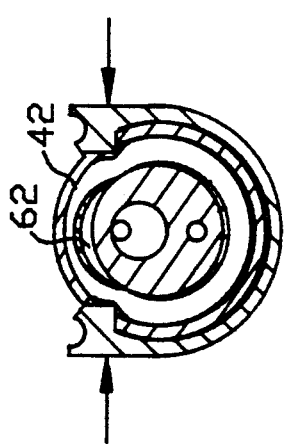
FIG. 4 is a view like FIG. 3 showing the valve of the unit activated.

This release means comprises, as best seen in FIGS. 3 and 4, a generally U-shaped pincher member 52, which partially encircles the entire outer housing and includes inwardly directed fingers or grippers 54 and 56 adjacent the ends thereof. These fingers extend through openings 58 and 60 in the outer housing 26, and engage the surface of O-ring 46. These fingers have sharp edges which engage and grip the outer surface of the O-ring 46 when pressed inward as shown by the arrows at FIG. 4. This pressure forces the O-ring 46 to bow outward releasing the force thereof on the surface of the bladder or sleeve 42. This allows the sleeve 42 to cup upward, as shown in FIG. 4, forming a passage 62 beneath and beyond the O-ring 46 communicating with the outlet port 40. Thus, the O-ring 46 and the extended portion of bladder functions as a valve to enable the fluid in chamber 50 to flow out the outlet 24 to provide the bolus dosage.

Figure 5:
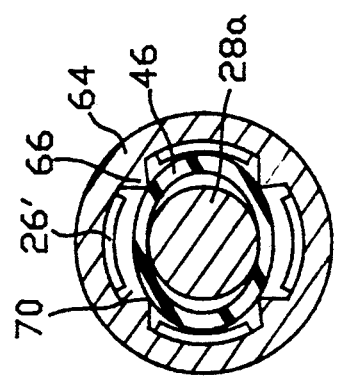
FIG. 5 is a section view like FIG. 3 of an alternate embodiment.

Referring to FIG. 5, an alternate embodiment of the valve activating or release means is illustrated and comprises a ring member 64 having inwardly directed wedge shaped fingers 66 extending through holes 70 in the outer housing 26' for engaging the O-ring 46. This arrangement has a more symmetrical construction and provides openings or passages on opposite sides of the central support member 28a.

In operation, a tubing set having an appropriate regulator is selected and connected to a source of IV fluid and to the patient. The patient (or user) receives a continuous background flow of medication until the prescribed period within which he may obtain a bolus dose if desired. If a bolus dose is desired, the user squeezes the actuator member 52 to release the accumulated dose from the bolus reservoir. Bolus adjustability may be achieved by moving O-ring 46 and the actuator 52 along member 28a.

Glass capillary tubes for mounting into cavities or chambers 32 and 35 are available from Beckton Dickenson Company on special order.

While we have illustrated and described our invention by means of specific embodiments, it should be understood that numerous changes and modifications may be made therein without departing from the spirit and scope of the invention as defined in the appended claims. We further assert and sincerely believe that the above specification contains a written description of the invention and the manner and process of making and using it, in such full, clear, concise, and exact terms as to enable any person skilled in the art to which it pertains, or with which it is most nearly concerned, to make and use the same, and further that it sets forth the best mode contemplated by us for carrying out the invention.

We claim:

1. An infusion system for the delivery of a first continuous flow of an intravenous fluid and second multiple selectable dosages of the fluid from a source to a site, comprising:
   a source of intravenous fluid under pressure;
   tubing means including a flow regulator for connecting said source of fluid to a delivery site; and
   said flow regulator comprising a housing having an inlet for connection to said source of fluid and an outlet for connection to a delivery site, first passage means in said housing communicating between said inlet and said outlet for conveying a continuous constant low volume of said fluid from said inlet to said outlet, and second passage means in the housing communicating between said inlet and said outlet independent of said first passage means having accumulator means for accumulating a predetermined fixed charge of fluid, and means for selectively releasing the flow of the fluid from the accumulator means to the outlet.

2. An infusion system according to claim 1 wherein said accumulator means is an elastic bladder.

3. An infusion system according to claim 1 wherein said first passage means includes a capillary tube for establishing said continuous constant low volume of said fluid to said outlet.

4. An infusion system according to claim 3 wherein said second passage means includes flow restriction means for establishing a predetermined rate of flow to said accumulator means for accumulating a predetermined fixed charge of fluid.

5. An infusion system according to claim 1 wherein said second passage means includes flow restriction means for establishing a predetermined rate of flow to said accumulator means for establishing a predetermined time period for accumulating a predetermined fixed charge of fluid.

6. An infusion system for the delivery of a first continuous flow of an intravenous fluid and second multiple selectable dosages of the fluid from a source to a site, comprising:
   a source of intravenous fluid under pressure;
   tubing means including a flow regulator for connecting said source of fluid to a delivery site;
   said flow regulator comprising a housing having a generally tubular outer shell and an axially extending inner cylindrical support member defining an annular chamber, an inlet for connection to said source of fluid and an outlet for connection to a delivery site, first passage means in said housing for conveying a continuous constant low volume of said fluid to said outlet, and second passage means in the housing having accumulator means for accumulating a predetermined fixed charge of fluid and means for selectively releasing the flow of the fluid from the accumulator means to the outlet; and
   said accumulating means comprising an elastic bladder defined by a tubular sleeve mounted on said cylindrical support member and confined without said tubular housing.

7. An infusion system according to claim 6 wherein:
   said elastic tubular sleeve is secured on said cylindrical support member by means of a pair of spaced apart end O-rings and an intermediate O-ring; and
   said means for selectively releasing the flow comprises means for deforming the intermediate O-ring for enabling fluid to pass beneath portions of said intermediate O-ring.

8. A infusion system according to claim 7 wherein said means for deforming the intermediate O-ring comprises means at least partially encircling said housing and having spaced apart finger means extending into said housing for engaging and deforming said intermediate O-ring in response to pressure thereon.

9. An infusion system according to claim 7 wherein said second passage mans is formed in said axially extending inner cylindrical support member and includes a passage communicating from said inlet to a surface thereof between a first of said end O-rings and said intermediate O-ring, and an outlet passage communicating from said surface thereof between a second of said O-rings and said intermediate O-ring to said outlet port.

10. An infusion system for the delivery of a first continuous flow of an intravenous fluid and second multiple selectable dosages of the fluid from a source to a site, comprising:
a source of intravenous fluid under pressure;
tubing means including a flow regulator for connecting said source of fluid to a delivery site;
said flow regulator comprising a housing having an inlet for connection to said source of fluid and an outlet for connection to a delivery site, first passage means in said housing communicating between siad inlet and said outlet for conveying a continuous constant low volume of said fluid to said outlet, and second passage means in the housing communicating between said inlet and said outlet independent of said first passage means, having an elastic bladder for accumulating a predetermined fixed charge of fluid and means for selectively releasing the flow of the fluid from the accumulator means to the outlet.

11. An infusion system for the delivery of a first continuous flow of an intravenous fluid and second multiple selectable dosages of the fluid from a source to a site, comprising:
a source of intravenous fluid under pressure;
tubing means including a flow regulator for connecting said source of fluid to a delivery site;
said flow regulator comprising a housing having an inlet for connection to said source of fluid and an outlet for connection to a delivery site, first passage means in said housing for conveying a continuous constant low volume of said fluid to said outlet, and second passage means in the housing having an elastic bladder for accumulating a predetermined fixed charge of fluid and means for selectively releasing the flow of the fluid from the accumulator means to the outlet, said housing having a generally tubular outlet shell and an axially extending inner cylindrical support member defining an annular chamber; and
said elastic bladder comprises a tubular sleeve mounted on said cylinder support member and confined within said tubular housing.

12. An infusion system according to claim 11 wherein:
said elastic tubular sleeve is secured on said cylindrical support member by means of a pair of spaced apart end O-rings and an intermediate O-ring; and
said axially extending inner cylindrical support member includes a passage communicating from said inlet to said sleeve between a first of said end O-rings and said intermediate O-ring, and an outlet passage communicating from said sleeve between a second of said end O-rings and said intermediate O-ring to said outlet port.

13. An infusion system according to claim 12 wherein said means for selectively releasing the flow comprises means for deforming the intermediate O-ring for enabling fluid to pass beneath portions of said intermediate O-ring and said sleeve.

14. An infusion system according to claim 13 wherein said means for deforming the intermediate O-ring comprises means at least partially encircling said housing and having spaced apart finger means extending into said housing for engaging and deforming said intermediate O-ring in response to pressure thereon.

15. An infusion system according to claim 14 wherein said first passage means includes a capillary tube for establishing said continuous constant low volume of said fluid to said outlet; and
said second passage means includes flow restriction means for establishing a predetermined rate of flow to said accumulator means for accumulating a predetermined fixed charge of fluid.

16. An infusion system for the delivery of a first continuous flow of a fluid and second multiple selectable dosages of an intravenous fluid from a source to a site, a flow regulator comprising:
a housing having an inlet for connection to a source of fluid and an outlet for connection to a delivery site;
first passage means in said housing for conveying a continuous constant low volume of said fluid from said inlet to said outlet; and
second passage means in the housing independent of siad first passage means having accumulator means for accumulating a predetermined fixed charge of fluid and means for selectively releasing the flow of the fluid from the accumulator means to the outlet.

17. An infusion system for the delivery of a first continuous flow of a fluid and second multiple selectable dosages of an intravenous fluid from a source to a site, a flow regulator comprising:
a housing having an inlet for connection to a source of fluid and an outlet for connection to a delivery site;
first passage means in said housing for conveying a continuous constant low volume of said fluid to said outlet; and
second passage means in the housing having accumulator means for accumulating a predetermined fixed charge of fluid and means for selectively releasing the flow of the fluid from the accumulator means to the outlet, said housing has a generally tubular outer shell and an axially extending inner cylindrical support member defining an annular chamber, said accumulator means comprising an elastic tubular sleeve secured on said cylindrical support member by means of a pair of spaced apart end O-rings and an intermediate O-ring, and said axially extending inner cylindrical support member includes a passage communicating from said inlet to said sleeve between said first O-ring and said intermediate O-ring, and an outlet passage communicating from said sleeve between said second O-ring and said intermediate O-ring to said outlet port.

18. An infusion system according to claim 17 wherein said means for selectively releasing the flow comprises means at least partially encircling said housing and having spaced apart finger means extending into said housing for engaging and deforming the intermediate O-ring for enabling fluid to pass beneath portions of said intermediate O-ring and said sleeve.

19. An infusion system according to claim 18 wherein said first passage means includes a capillary tube for establishing said continuous constant low volume of said fluid to said outlet; and
said second passage means includes flow restriction means for establishing a predetermined rate of flow to said accumulator means for accumulating a predetermined fixed charge of fluid.

* * * * *